United States Patent [19]

Ohnaka et al.

[11] Patent Number: 5,045,185
[45] Date of Patent: Sep. 3, 1991

[54] BLOOD SEPARATOR FOR SEPARATING BLOOD COMPONENTS FROM A BLOOD BAG INTO SEPARATION BAGS

[75] Inventors: Yukihiro Ohnaka; Takao Iwasa, both of Fujinomiya; Tatsumiko Kawaoka, Takatsuki, all of Japan

[73] Assignee: Terumo Kabushiki Kaisha, Tokyo, Japan

[21] Appl. No.: 360,883

[22] PCT Filed: Nov. 10, 1987

[86] PCT No.: PCT/JP87/00866

§ 371 Date: Jun. 23, 1989

§ 102(e) Date: Jun. 23, 1989

[87] PCT Pub. No.: WO88/03418

PCT Pub. Date: May 19, 1988

[30] Foreign Application Priority Data

Nov. 10, 1986 [JP] Japan .................. 61-265588
Nov. 10, 1986 [JP] Japan .................. 61-265589

[51] Int. Cl.$^5$ .................. B01D 21/36; B01D 21/30
[52] U.S. Cl. .................. 210/86; 210/85; 210/94; 210/109; 210/143; 210/513; 222/52; 222/96; 222/103; 222/214
[58] Field of Search .................. 210/86, 94, 109, 141, 210/143, 205, 513, 514, 515, 744, 745; 222/23, 52, 95, 96, 103, 214

[56] References Cited

U.S. PATENT DOCUMENTS

| | | | |
|---|---|---|---|
| 4,040,959 | 8/1977 | Berman et al. ............... | 210/782 |
| 4,294,320 | 10/1981 | Bilstad et al. ............... | 177/1 |
| 4,350,585 | 9/1982 | Johansson et al. ........... | 210/96.1 |
| 4,354,116 | 10/1982 | Tsukamoto et al. .......... | 250/576 |
| 4,378,854 | 4/1983 | Rosen ......................... | 177/118 |
| 4,663,032 | 5/1987 | Loos et al. ................... | 210/97 |
| 4,976,851 | 12/1990 | Tanokura et al. ............ | 210/86 |

FOREIGN PATENT DOCUMENTS

| | | |
|---|---|---|
| 0161551 | 11/1985 | European Pat. Off. . |
| 55-17585 | 5/1980 | Japan . |
| 57-30507 | 6/1982 | Japan . |
| 60-148562 | 8/1985 | Japan . |
| 62-64369 | 3/1987 | Japan . |
| 84/00492 | 2/1984 | PCT Int'l Appl. . |
| 2046612 | 11/1980 | United Kingdom . |

Primary Examiner—W. Gary Jones
Attorney, Agent, or Firm—Staas & Halsey

[57] ABSTRACT

A blood separator having: a blood bag pressurizing section for retaining a centrifuged blood bag and pressurizing the same at a predetermined pressure; a retention/measurement section for retaining at least two separation bags connecting with the blood bag via tubes and capable of receiving separated blood components, and measuring the weight of the separation bags; limiting devices provided at intermediate portions of the tubes between the blood bag and the separation bags to limit the flows of liquids in the tubes; a detector for detecting the level of an interface between components of blood in the blood bag retained in the blood bag pressurizing section; a moving device for moving the detector relative to the blood bag; and a controller for controlling the limiting devices while receiving, as an item of control information, detection information from the detector and/or measurement information from the retention/measurement section.

12 Claims, 15 Drawing Sheets

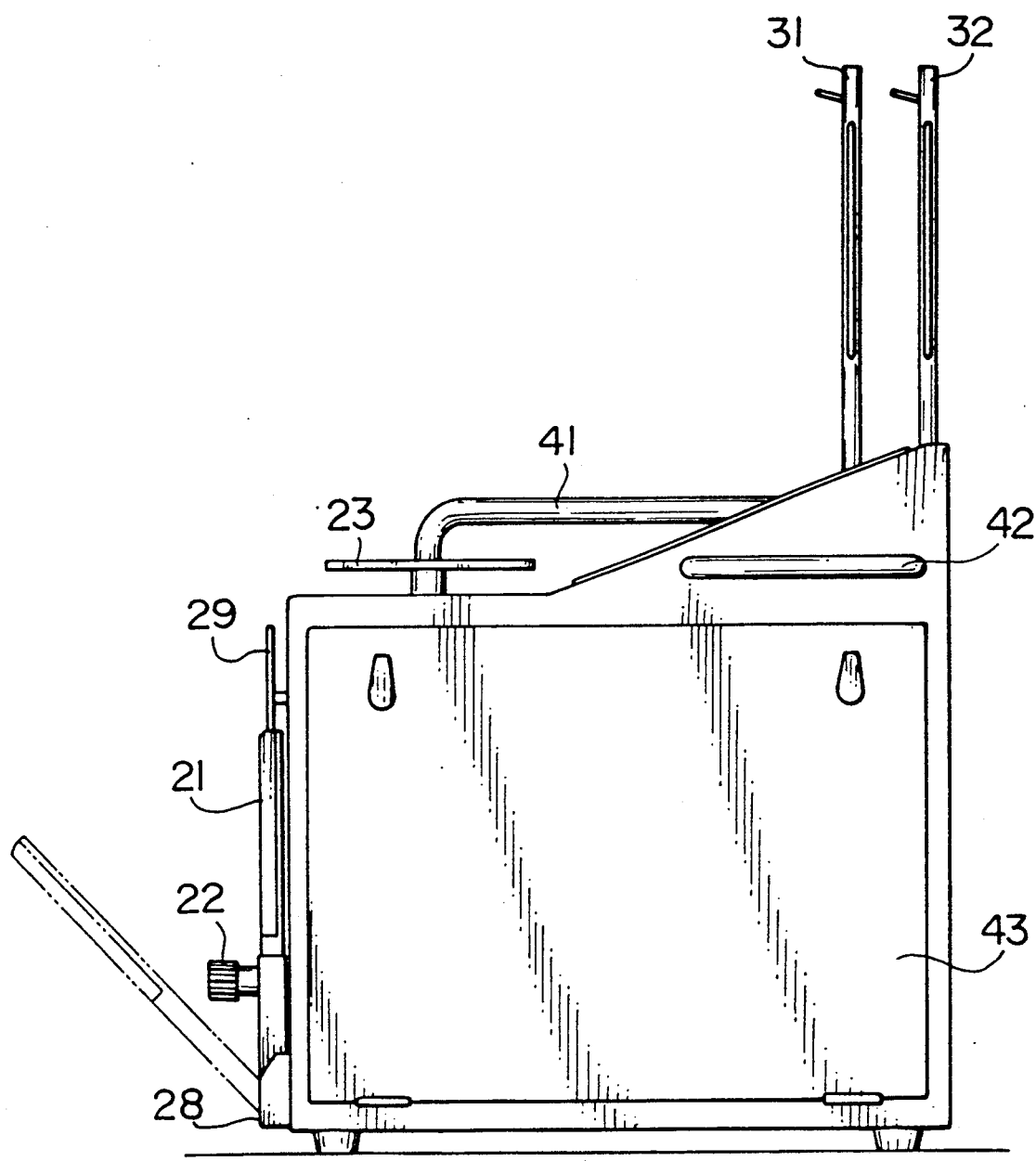
F I G. 1C

BLOOD SEPARATOR FOR SEPARATING BLOOD COMPONENTS FROM A BLOOD BAG INTO SEPARATION BAGS

TECHNICAL FIELD

This invention relates to a blood separator which automatically separates centrifuged component parts of blood contained in a blood bag by distributing the component parts to separation bags.

BACKGROUND ART

Recently, abuses associated with whole blood transfusion are becoming to be regarded as a serious problem, and component transfusion, whereby only the component parts of blood necessary for a patient are used for transfusion, is increasingly being adopted with a view to minimizing the physical burdens imposed on a patient and unfavorable side effects due to immunity and the like.

To make a component preparation, it is necessary to separate the component parts of blood in a blood bag by means of a centrifugal separator and to supply the component parts to respective separation bags.

In a conventional process, a separator stand such as that shown in FIG. 8 is used to manually separate centrifuged plasma in a blood bag and enclose the separated plasma by forming an enclosing portion in a tube extending from a separation bag.

That is, a blood bag 1 which has undergone centrifugation is set under vertically retaining pins 3 while blood corpuscles are prevented from rising. An intermediate portion of a tube extending from a separation bag 4 is previously closed by a clamp 6, and a separation needle 7 attached to the extreme end of the tube 5 is put through an outlet 1a of the blood bag 1 so that the two bags are connected with each other. A lever 8 of the separation stand 2 is then disengaged from a hook 9. The lever 8 that is constantly forced by a spring (not shown) in the desired direction thereby pinches the blood bag 1 between a swingable pressurizing plate 11 and a stationary plate 10 of the separation stand 2. At the same time, the clamp 6 closing the intermediate portion of the tube 5 is removed, thereby allowing plasma to be separately supplied to the separation bag 4. When blood corpuscles star entering the tube 5 after the plasma has moved to the separation bag 4, the tube 5 is closed by the clamp 6, the pressurizing plate 11 is returned, and the lever 8 is brought into engagement with the hook 9.

Thereafter, the separation bag 4 is pressed by hand and the clamp 6 is opened so as to discharge air toward the blood bag 1, and the tube 5 is closed by the clamp 6.

Conventionally, an ordinary separation process is based on manual operations, as described above, and entails the problems described below. 1) The burden imposed on the operator is considerable. That is to say, the separation operation is labor-intensive and is conducted one bag at a time. The number of bags simultaneously operated by one operator is at most two. The level of working efficiency is therefore low. 2) Such items of equipment as a separation stand, a balance and a tube sealer must be provided separately, and the space occupied by such equipment is considerable. 3) A high degree of skill and intuition are needed in controlling the quantity of each blood component part.

SUMMARY OF THE INVENTION

An object of the present invention is to provide a blood separator free from these problems.

The present invention therefore provides in one of its aspects a blood separator having: a blood bag pressurizing means for retaining a centrifuged blood bag and pressurizing the same at a predetermined pressure; a retention/measurement means for retaining at least two separation bags connecting with the blood bag via tube means and capable of receiving separated blood components, the retention/measurement means measuring the weight of the separation bags; a limiting means provided at intermediate portions of the tube means between the blood bag and the separation bags, the limiting means limiting the flows of liquids in the tube means; and a control means for controlling the limiting means while being supplied with information on the weight measured by the retention/measurement means as an item of control information.

The present invention provides in another of its aspects a blood separator having: a blood bag pressurizing means for retaining a centrifuged blood bag and pressurizing the same at a predetermined pressure; a bag retaining means for retaining at least two separation bags connecting with the blood bag via a tube means and capable of receiving separated blood components; a limiting means provided at intermediate portions of the tube means between the blood bag and the separation bags retained by the retaining means, the limiting means limiting the flows of liquids in the tube means; a detection means for detecting the level of an interface between components of blood in the blood bag retained by the blood bag pressurizing means; a moving means for moving the detecting means relative to the blood bag; and a control means for controlling the limiting means while being supplied with detection information from the detection means as an item of control information.

The present invention provides in still another of its aspects a blood separator having: a blood bag pressurizing means for retaining a centrifuged blood bag and pressurizing the same at a predetermined pressure; a retention/measurement means for retaining at least two separation bags connecting with the blood bag via tube means and capable of receiving separated blood components, the retention/measurement means measuring the weight of the separation bags; a limiting means provided at intermediate portions of the tube means between the blood bag and the separation bags, the limiting means limiting the flows of liquids in the tube means; a detection means for detecting the level of an interface between components of blood in the blood bag retained by the blood bag pressurizing means; a moving means for moving the detecting means relative to the blood bag; and a control means for controlling the limiting means while being supplied with detection information from the detection means and/or measurement information from the retention/measurement means as an item of control information.

The control means controls the limiting means by receiving detection information supplied as an item of control information from the detection means, and thereby automatically stores the component parts in the respective separation bags.

The control means controls the limiting means by receiving information on the weight measured by the retention/measurement means as an item of control information, and thereby automatically stores the component parts in the respective separation bags.

The control means controls the limiting means by receiving, as an item of control information, detection information from the detection means and/or measured weight information from the retention/measurement means, and thereby automatically stores the component parts in the respective separation bags.

BRIEF DESCRIPTION OF THE DRAWINGS

FIGS. 1A to 1C are diagrams of the appearance of an embodiment of the present invention;

BEST MODE FOR CARRYING OUT THE INVENTION

A preferred embodiment of the present invention will be described below with reference to the accompanying drawings.

Figure 1A:
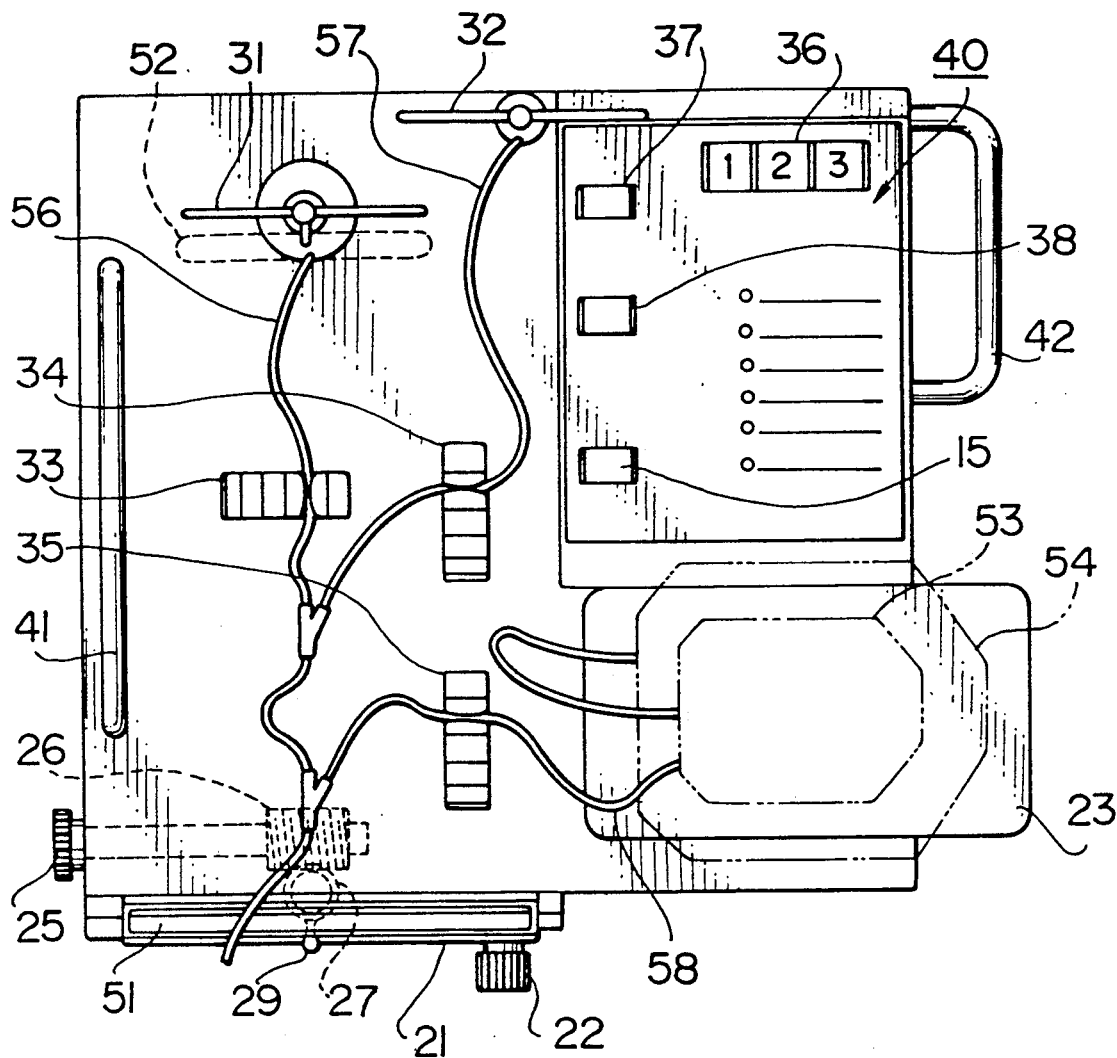
Figure 1B:
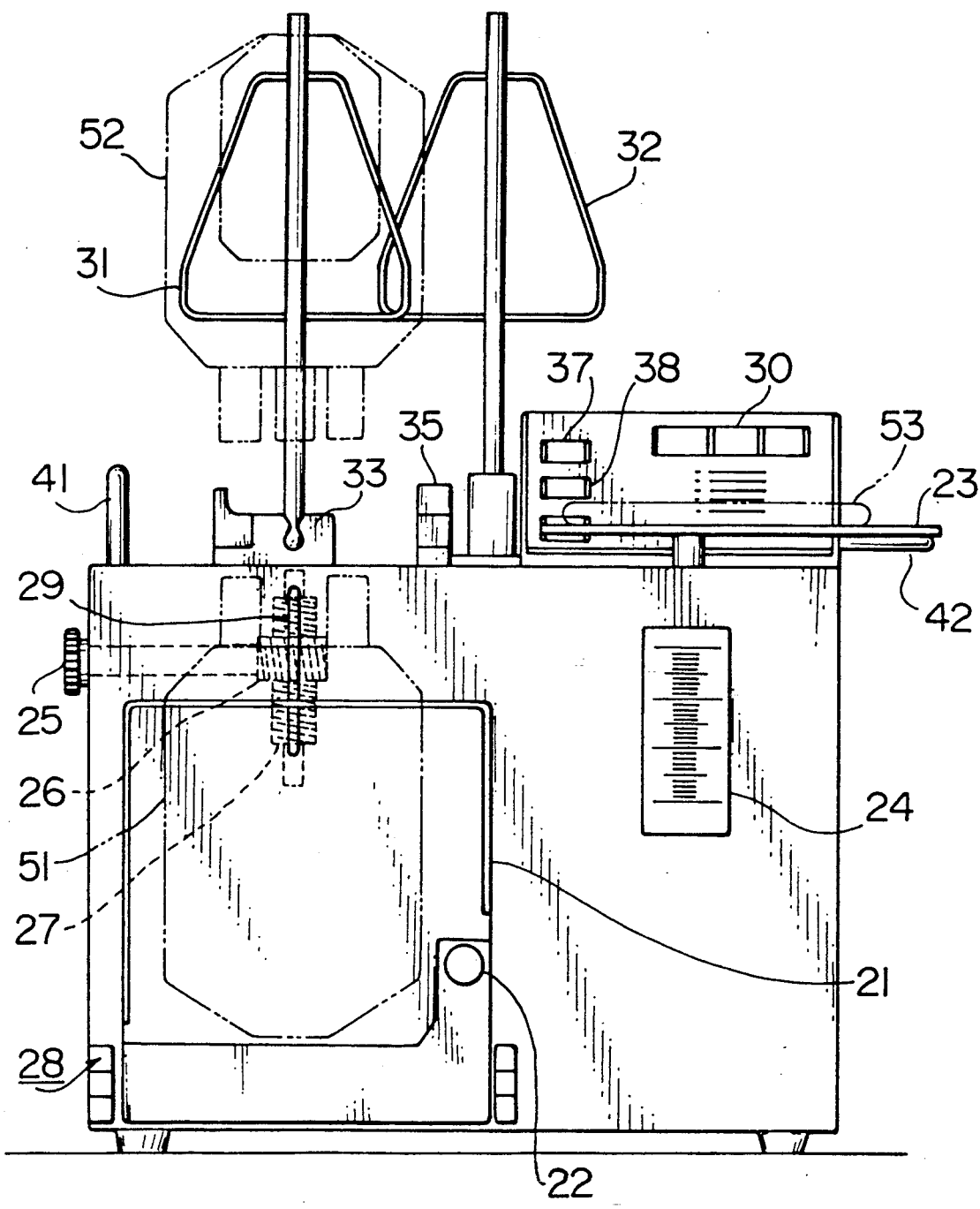

FIGS. 1A to 1C are a plan view, a front view and a side view of an embodiment of the present invention, illustrating the appearance thereof.

Referring to FIGS. 1A to 1C, a pressurizing plate 21 for pressurizing a blood bag 51, a stopper 22 for limiting the movement of the pressurizing plate 21, a measurement plate 23, a weight scale window 24 through which a measured value of the weight of an object placed on the measurement plate 23 is indicated are illustrated. The weight of the object on the measurement plate 23 is measured by a spring balance mechanism having parallel links and incorporating a rotary encoder which outputs a signal having a value proportional to the measured weight.

An adjustment knob 25 is used to adjust the position of a photosensor 29 in the vertical direction. A worm gear 26 is fixed to a rotary shaft connected to the adjustment knob 25. The worm gear 26 constantly meshes with a pinion gear 27 to which the photosensor 29 is secured. At a pressurization/retention section 28, the blood bag 51 is retained and pressurized with the pressurizing plate 21. The photosensor 29 is used to detect a concentrated red corpuscle portion of blood in the blood bag 51 suspended from hook pins (not shown) of the pressurization/retention section 28.

A separation bag is suspended from a hanger 31. A spring balance mechanism having parallel links is constructed below the hanger 31. A rotary encoder incorporated in the balance mechanism outputs a signal having a value proportional to the measured weight of the separation bag suspended from the hanger 31. Another hanger 32 is provided from which a separation bag optionally used is suspended. Each of clamp valves 33 to 35 is operated to control the flow of a liquid in a tube by fastening a tube sealer. When the valve is closed, the liquid flow is stopped. An operational panel 40 is provided with a power switch 15, a select switch 36 for selecting one of different operational modes, a start switch 37, and a stop switch 38. Handles 41 and 42 and a maintenance panel 43 are also provided. Bags 51 to 54 which receive component parts of blood may also be attached to the hanger 32 if necessary.

Figure 2A:
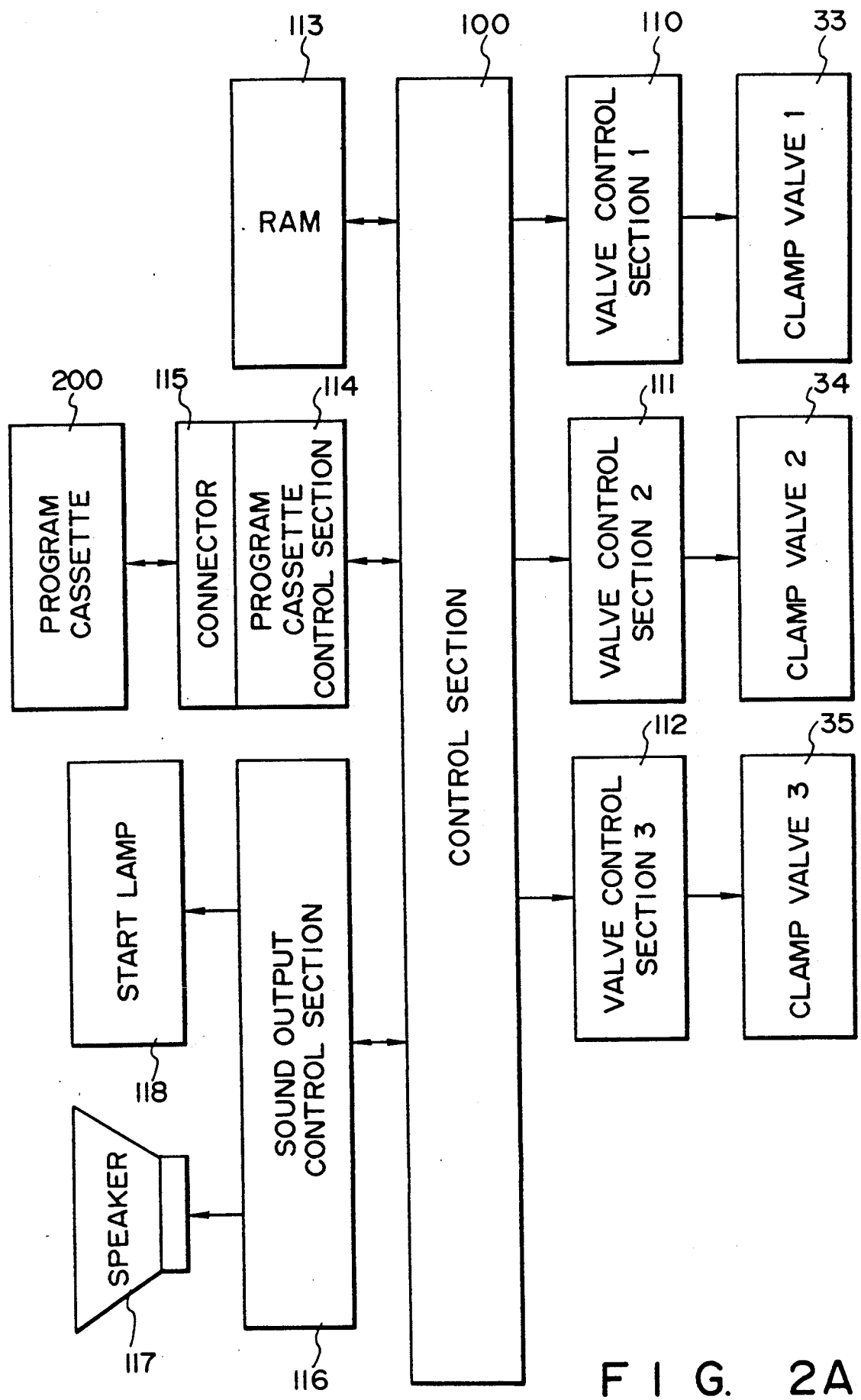
FIG. 2A and 2B are block diagrams of this embodiment.
Figure 2B:
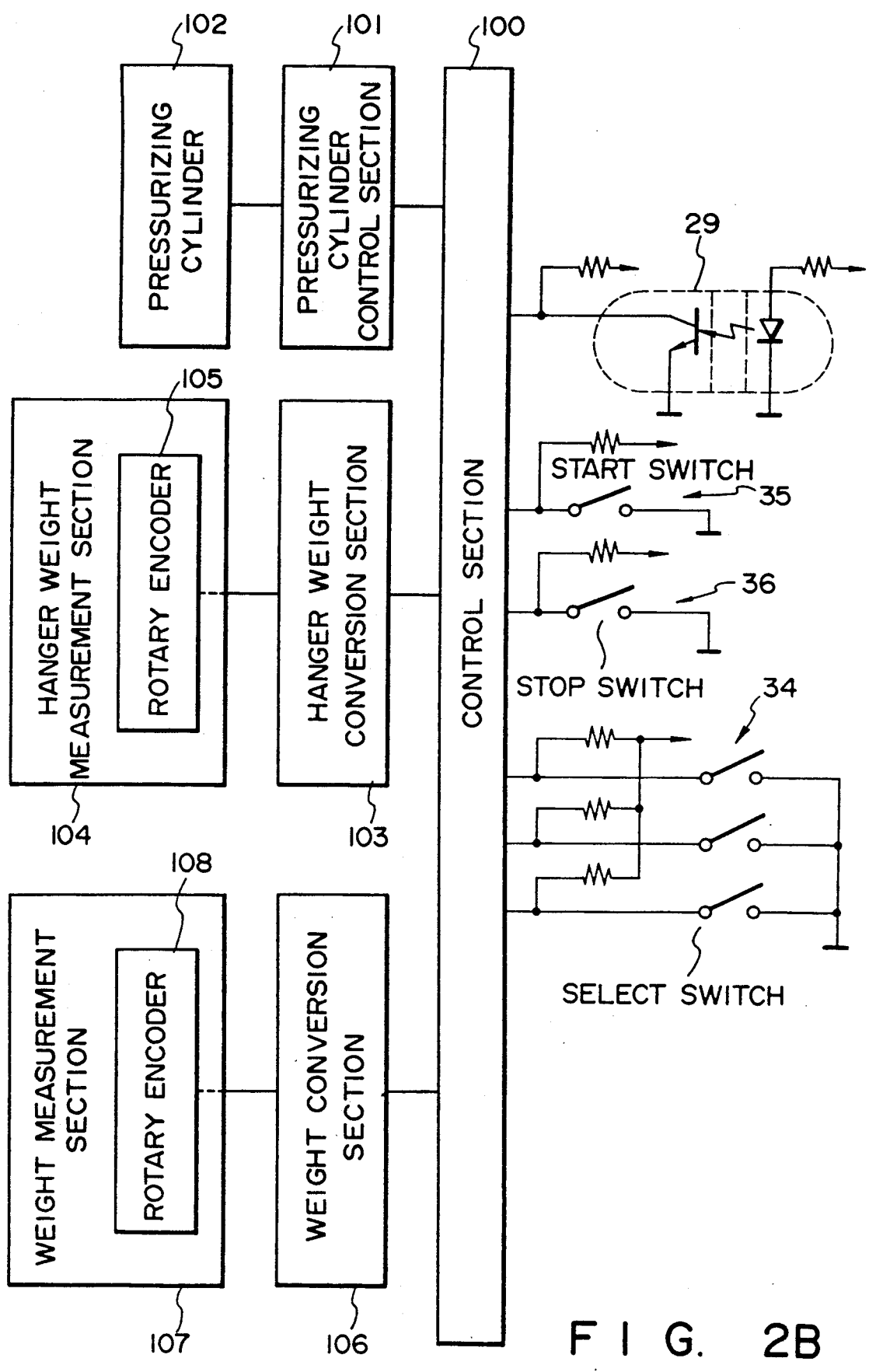

The construction of an electric control section of this embodiment will be described below with reference to block diagrams of FIGS. 2A and 2B.

A control section 100 controls the overall operation of this embodiment in accordance with a program stored in a program cassette 200 attached to a connector 115 of a program cassette control section 114. A pressurizing cylinder control section 101 controls a pressurizing cylinder 102 which maintains the pressurizing plate 21 in a non-pressurizing state against the pressure of a spring (not shown). The pressurizing plate 21 pressurizes a set bag by the force of this spring when the pressurizing cylinder 102 is not actuated. A hanger weight conversion section 103 calculates the weight of a bag suspended from the hanger 31 from a signal which is output from a rotary encoder 105 of a weight measurement section 104 provided below the hanger 31 and which has a value proportional to the weight of the bag, the hanger weight conversion section 103 then outputs a calculated value to the control section 100. A weight conversion section 106 calculates the weight of a bag placed on the measurement plate 23 from a signal which is output from a rotary encoder 108 and which has a value proportional to the weight of the bag measured by a weight measurement section 107, and the weight conversion section 106 outputs a calculated value to the control section 100.

Valve control sections 110 to 112 control opening/closing of the clamp valves 1 to 3 (33 to 35). A RAM 113, a sound output control section 116 for driving a speaker or controlling sound outputs from the speaker, e.g., a chime sound, the photosensor 29 and the switches 36 to 38 are also connected to the control section 100.

OPERATION

Figure 3A:
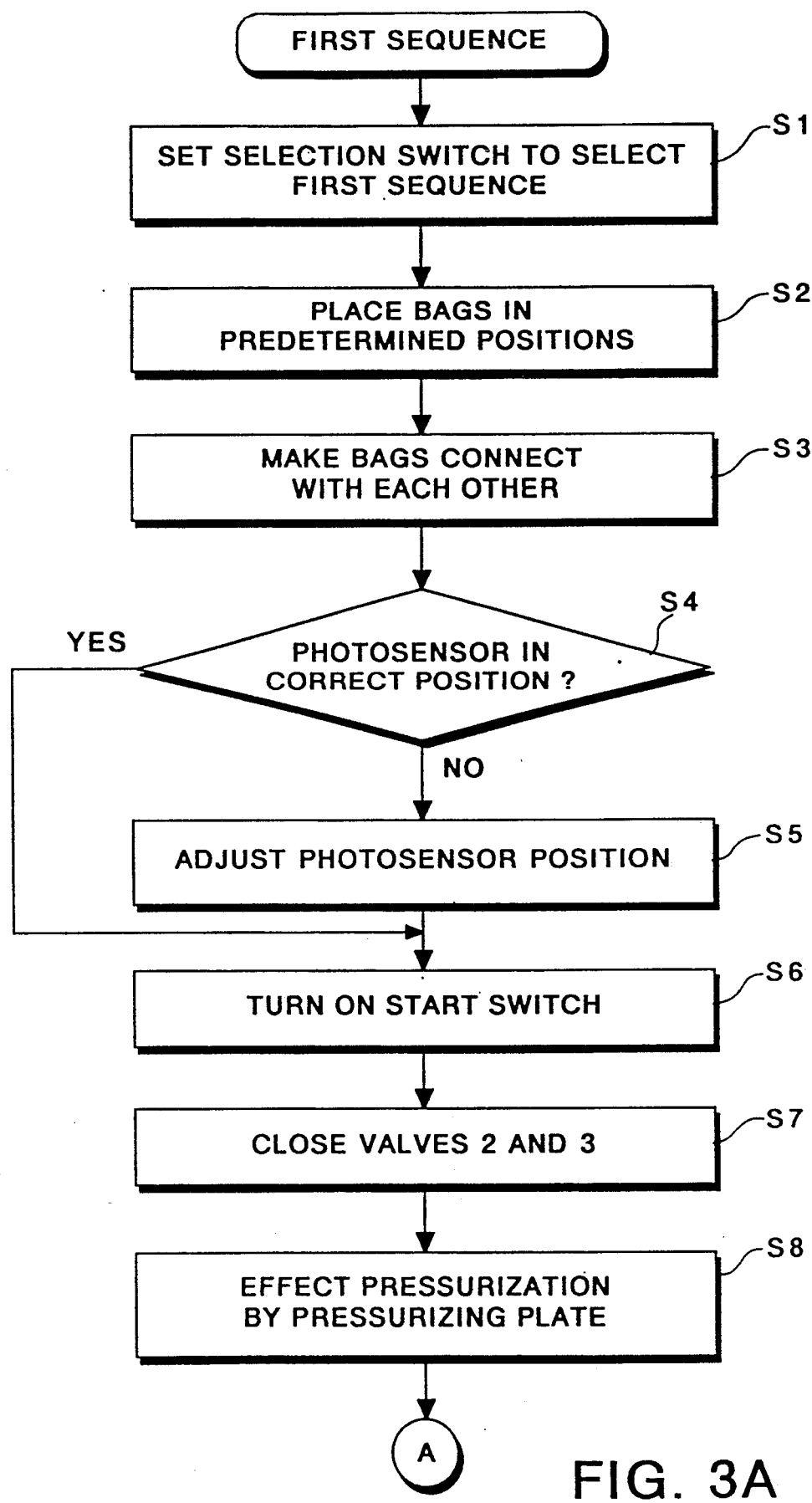
FIGS. 3A to 3C are flow charts of a first sequence of the embodiment
Figure 3B:
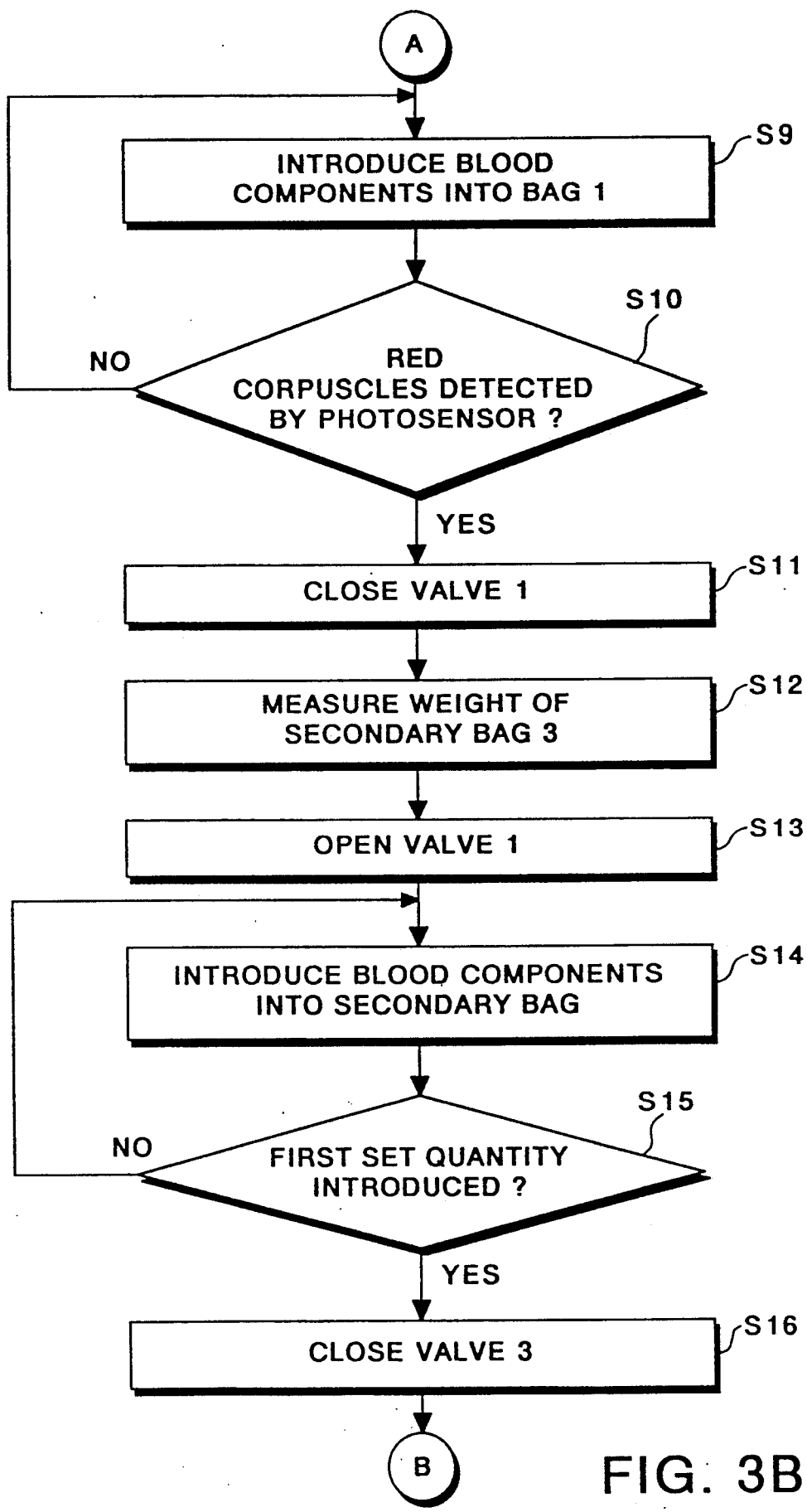
Figure 3C:
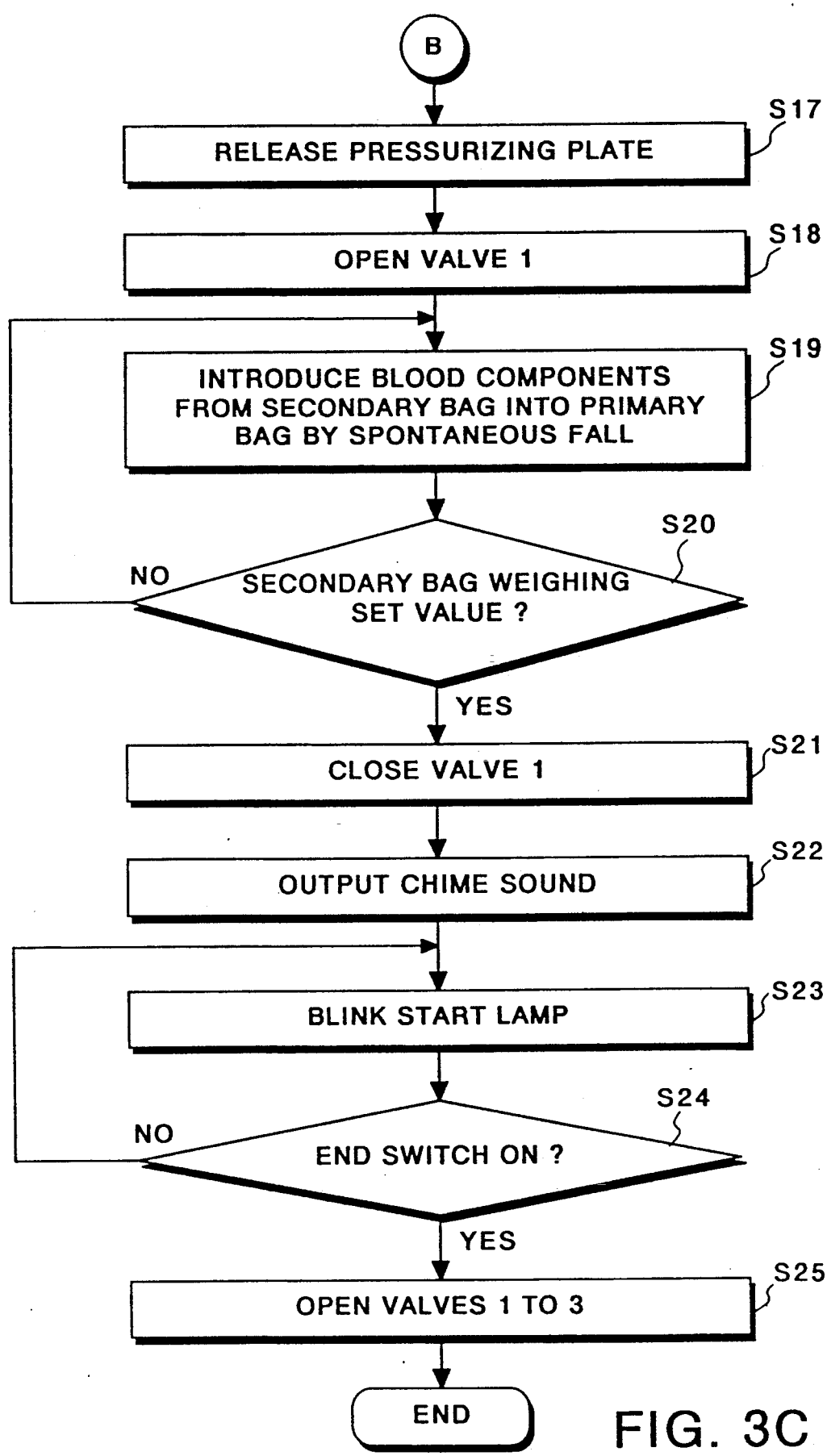

A process of control effected by the thus-constructed embodiment will be described below with specific reference to the flow charts of FIGS. 3A to 3C.

In step S1, a key "1" of the select switch 36 is selected to select a first sequence. In step S2, bags are thereafter set in respective positions. In this case, a blood bag 51 which has undergone strong centrifugation (e.g., at 1700 to 5500 G for 4 to 10 minutes) is set inside the pressurizing plate 21, a secondary bag 1 (52) is suspended from the hanger 31 and a secondary bag 3 (53) and a tertiary bag (54) are placed on the measurement plate 23. In step S3, communication is provided between the secondary and tertiary bags and the blood bags by tubes extending through the clamp valves 1 and 3 (33 and 35), as shown in FIG. 1A, although no tube is provided between the hanger 32 and the clamp valve 2 (34) in this case.

Figure 4:
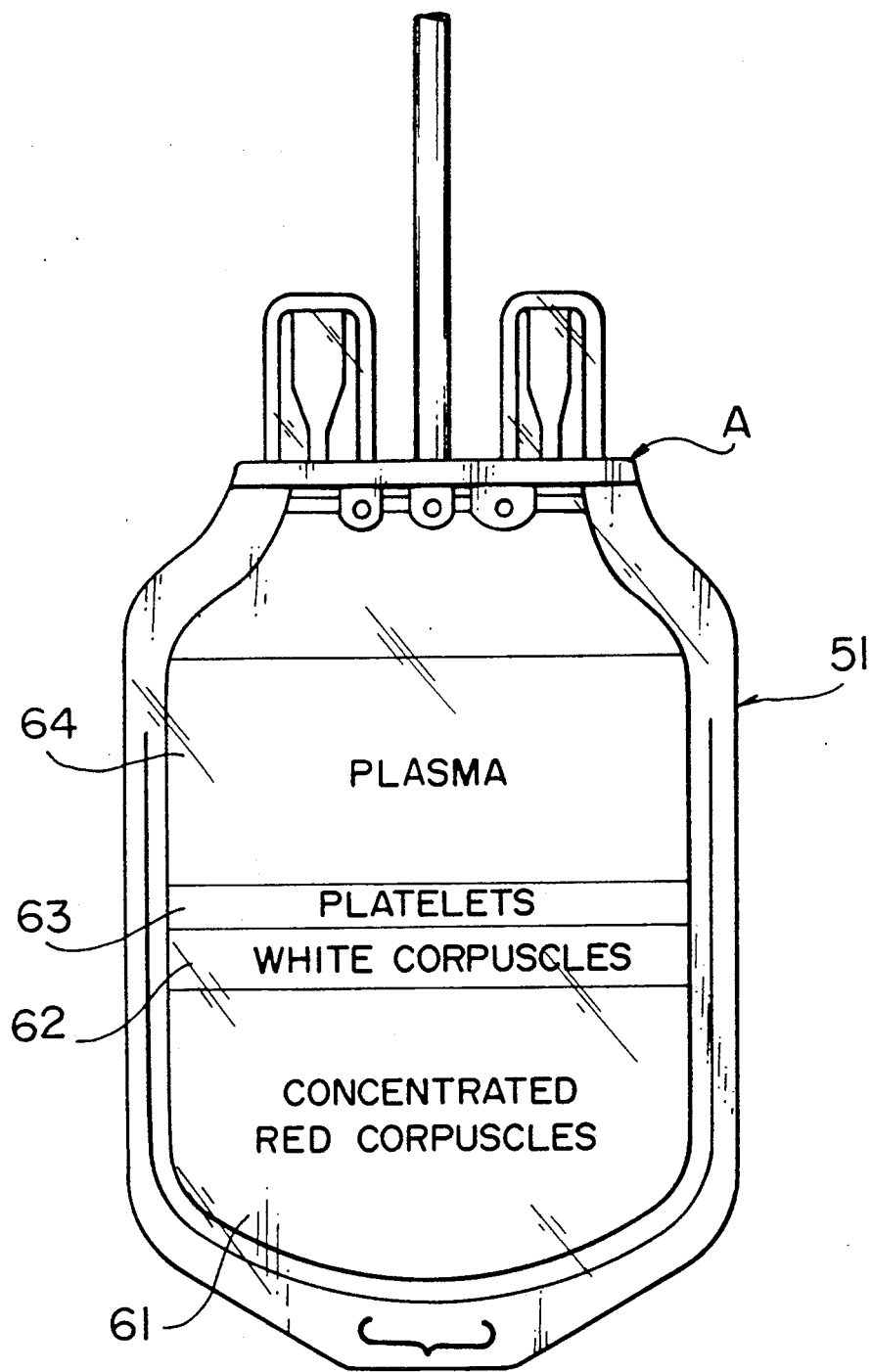
FIG. 4 is a diagram of a state of a blood bag which has undergone strong centrifugation.

The component parts of blood in the blood bag 51 are separate from each other, as shown in FIG. 4. That is, a concentrated red corpuscle layer 61 is formed at the bottom, a white corpuscle layer 62 is formed over the layer 61, a platelet layer 63 is formed over the layer 62, and a plasma layer 64 is formed at the highest position.

In step S4, check is made to determine whether or not the detection position of the photosensor 29 is approximately at a predetermined height (e.g., about 32 mm) from an upper surface of the blood bag 51 (position A shown in FIG. 4) after the blood bag 51 has been suitably set at the position of the pressurizing plate 21. If the photosensor 29 is not at the predetermined position, the photosensor 29 is moved in the vertical direction in step S5 by rotating the adjustment knob 25 so as to adjust the photosensor 29 to the desired position, and the process then proceeds to step S6. Since light can be transmitted through the plasma layer 64, supply of the blood content to the secondary bag 1 (52) can be controlled so that the content is discharged until the photosensor 29 detects the concentrated red corpuscle layer 61, thereby enabling the user to adjust the amount of supplied liquid.

Preparation for blood separation is thereby completed. Then, in step S6, the start switch 37 is depressed to input a starting signal. In step S7, the clamp valve 2 (34) and the clamp valve 3 (35) are closed to inhibit the liquid from flowing through the set tubes. The flows into the secondary bag 2 (not set, in this example) and the secondary bag 3 (53) are thereby stopped. In step S8, a command to stop actuation of the pressurizing cylinder is issued to the pressurizing cylinder control section 101, thereby allowing the pressurizing plate 21 to squeeze (press) the blood bag 51 by the pressure of the pressurizing plate spring. Consequently, in step S9, the blood content in the blood bag 51 is transported to the secondary bag 1 (52) via the clamp valve 1 (33) in an open state. In step S10, whether or not the photosensor 29 has detected the concentrated red corpuscle layer 61 is checked. If NO, completion of detection is awaited. After the red corpuscle level in the blood bag 51 has been detected by the photosensor 29, the process proceeds from step S10 to step S11, and a command to close the clamp valve 1 (33) is issued to the valve control section 110, thereby stopping the flow into the secondary bag 1 (52). As a result, only the plasma layer 64 in the blood bag 51 is transported to the secondary bag 1 (52).

In step S12, the weight of the secondary bag 3 (53) and the tertiary bag (54) that are placed on the measurement plate 23 and that are vacant is measured (weight data is read from the weight conversion section 106), and the value of the weight is stored in the RAM 113. In step S13, the valve control section 3 (112) is controlled so as to open the clamp valve 3 (35) and, in step S14, the blood content in the blood bag 51 is thereby transported to the secondary bag 3 (53). The control section 100 monitors the measured weight output from the weight conversion section 106, and checks whether or not a quantity of blood content corresponding to a first set value (e.g., 70 g) designated from the program cassette 200 has entered the bag (or whether or not the weight of the bag has increased). After transportation of the first set quantity has been completed, the process proceeds to step S16, and the valve control section 3 (112) is controlled so as to close the clamp valve 3 (35), thereby stopping the flow into the secondary bag 3 (53). Thereafter, in step S17, the pressurizing cylinder control section 101 is controlled so as to actuate the pressurizing cylinder 102 to open the pressurizing plate 21. The secondary bag 3 (53) is thereby supplied with platelets, part of white and red corpuscles and the rest of plasma.

In step S18 the valve control section 1 (110) is controlled so as to open the clamp valve 1 (33) and, in step S19, the blood content (plasma) is thereby allowed to flow from the secondary bag 1 (52) into the primary bag, i.e., the blood bag 51 by spontaneous fall. Then, in step S20, the weight of the secondary bag 1 (52) suspended from the hanger 31 is read from the hanger weight conversion section 103, and whether or not a quantity of liquid corresponding to a set bag weight (e.g., 20 g) designated from the program cassette 200 has entered the blood bag 51 is monitored. After the set value has been reached, the process proceeds to step S21, and the valve control section 110 is controlled so as to close the clamp valve 1 (33), thereby stopping the flow into the blood bag 51.

Thus, the predetermined quantity of plasma flows into the concentrated red corpuscles remaining in the blood bag 51. As a result, the hematocrit value of the concentrated red corpuscle liquid can be corrected to, for example, 80% or less.

Separation of the blood components is thus completed and, in steps S22 and S23, the sound output control section 116 is controlled so as to output a chime sound from the speaker 117 several times as well as to blink the start lamp 118 (illumination portion of the illumination type of start switch 37). The operator thereby recognizes that the process of separating the blood components has been completed. The operator then pinches the tubes used for connection between the bags by clips or the like so as to close the tubes, and thereafter depresses the end switch 38 to input an ending signal. In response to this input monitored by the control section 100, the process proceeds to step S25, and the valve control sections 110 to 112 are controlled so as to open the clamp valves 33 to 35, thereby terminating the process.

In the above description, the present invention is exemplified with respect to the case where the secondary bag 2 is not suspended from the hanger 32. The secondary bag 2 may be used in such a manner that an additive liquid for preservation of blood to be supplied to the blood bag as desired is contained in the secondary bag 2, and a predetermined quantity of the additive liquid is supplied to the blood bag 51 after step S17. Of the blood component parts separated and distributed in the blood bag 51 and the secondary bags 1 (52) and 3 (53), concentrated red corpuscles 61, white corpuscles 62 and platelets 63 and part of plasma 64 can be separated more finely.

To perform this operation, the secondary bag 3 (53) is subjected to weak centrifugation. For example, weak centrifugation is effected at 800 G for 5 minutes. After this processing, the content of the secondary bag 3 (53) is in a state such as that illustrated in FIG. 5, and the upper most layer is a layer of liquid platelets 65. A quantity of liquid platelets can be obtained by such a light centrifugation.

Figure 5:
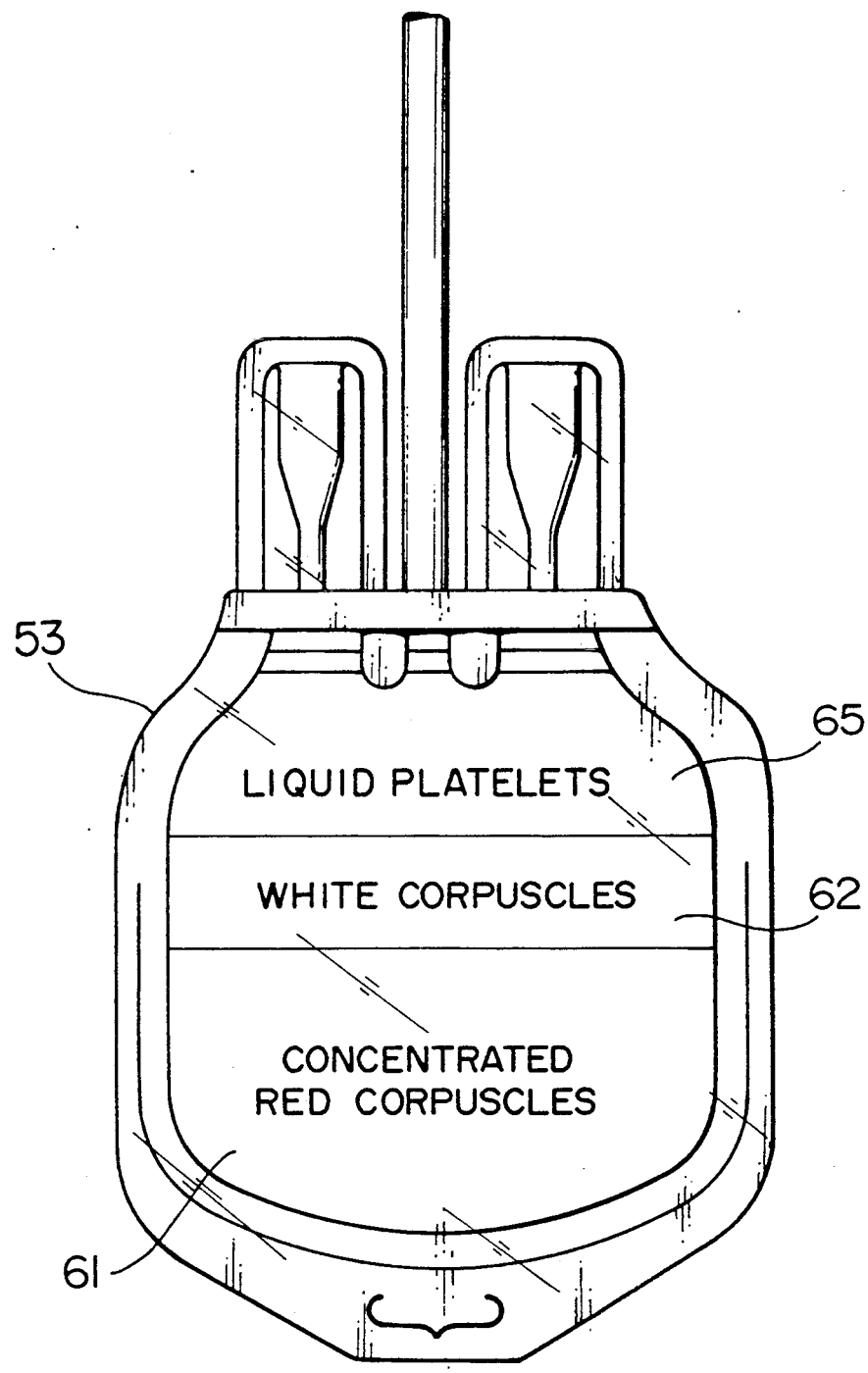
FIG. 5 is a diagram of a state of a secondary bag which has undergone light centrifugation after separation processing in accordance with the first sequence of the embodiment.
Figure 6A:
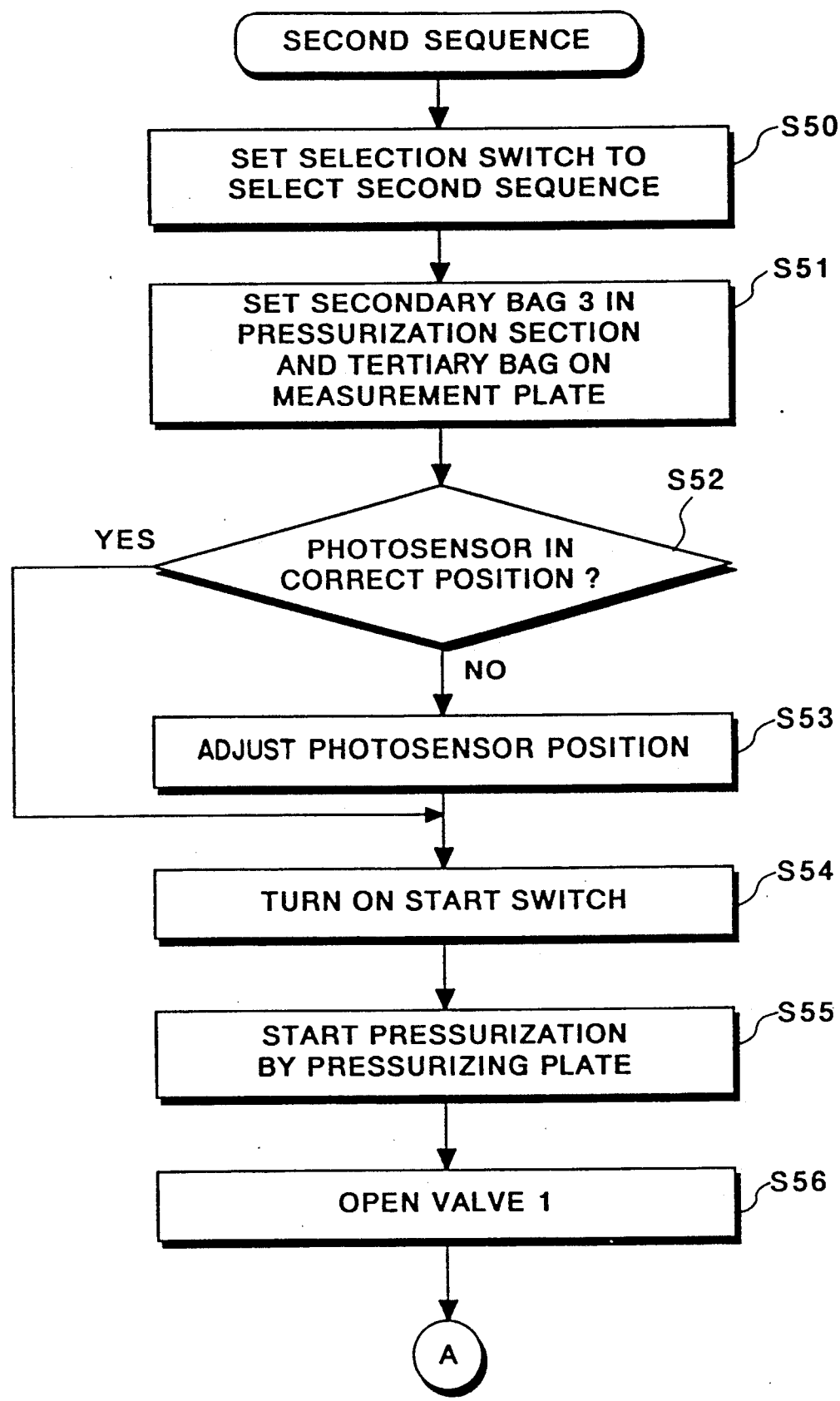
FIGS. 6A and 6B are flow charts of a second sequence of the embodiment.
Figure 6B:
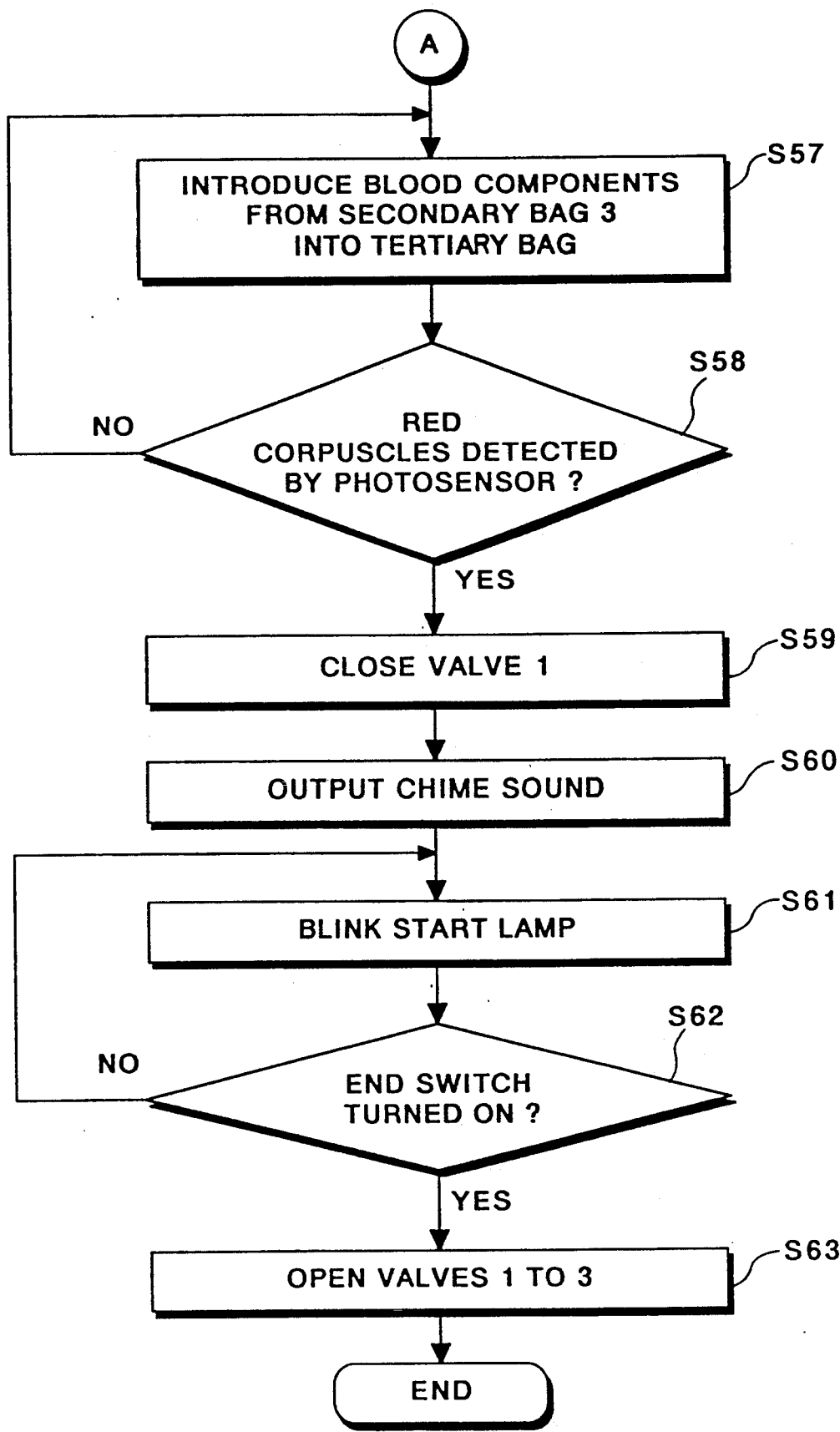

Thereafter, a process in accordance with a second sequence shown in FIGS. 6A and 6B may be executed. First, in step S50, a key "2" of the select switch 36 is depressed to select the second sequence. In step S51, the secondary bag 3 (53) in the state shown in FIG. 5 is set at the pressurizing plate 21, the tertiary bag (54) is placed on the measurement plate 33, and connection is provided between these bags by using a tube which is led through the clamp valve 3 (35). In step S52, whether or not the photosensor 29 is at the predetermined position is checked, as in the case of step S4. If NO, the adjustment knob 25 is rotated in step S53 to set the photosensor 29 to the desired position. The process then proceeds to step S54, and the start switch 37 is depressed and turned on. The control section 100 detects the on state of the start switch 37 and controls the pressurizing cylinder control section 101 to stop actuation of the pressurizing cylinder, so that the pressurizing plate 21 is pressed against the secondary bag 3 (53) by the force of the pressurizing plate spring (not shown). Then, in step S56, the clamp valve 3 (35) is opened, and the content liquid in the secondary bag 3 (53) is transported to the tertiary bag (54). In step S58, whether or not the photosensor 29 has detected red corpuscles is monitored. After the photosensor 29 has detected red corpuscles, the process proceeds to step S59, and the valve control section 110 is controlled so as to close the clamp valve 3 (35). In steps S60 to S62, chime sound is output, the start lamp 118 is made to blink, and the input given by pressing the end switch 38 is awaited, as in the case of steps S22 to S24. The operator presses the end switch after he has recognized the completion of the second sequence and performed necessary operations. Then, the process proceeds from step S62 to step S63, the clamp valve 1 is opened, and the process terminates.

This control process enables liquid platelets 65 to be separated alone from the mass of concentrated red corpuscles 61, white corpuscles 62 and liquid platelets 65.

The present invention has been described with respect to the case where the content liquid in the secondary bag 3 (53) is separated under the control using the photosensor 29. However, the embodiment apparatus is capable of effecting separation by utilizing weight measurement instead of sensing with the photosensor.

Figure 7A:
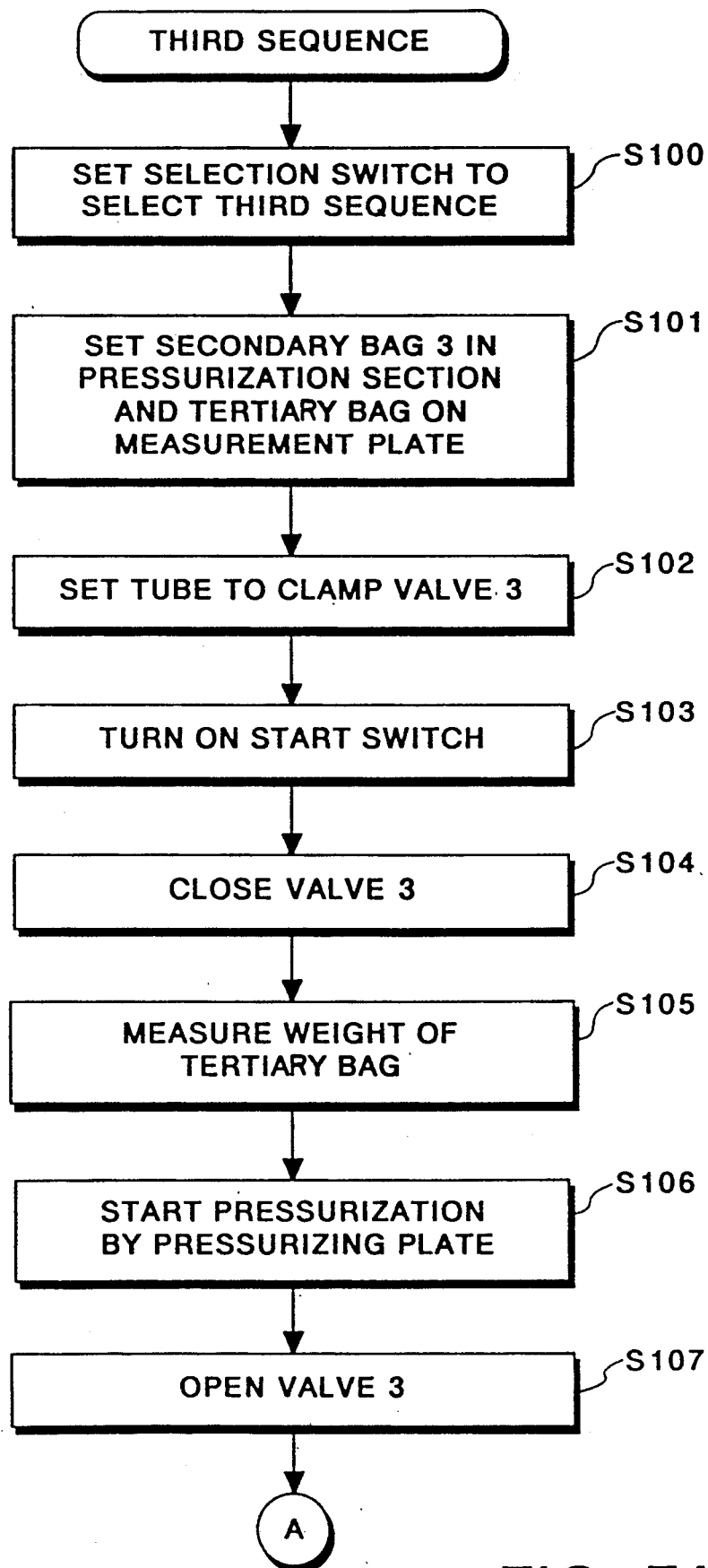
FIGS. 7A and 7B are flow charts of a third sequence of the embodiment.
Figure 7B:
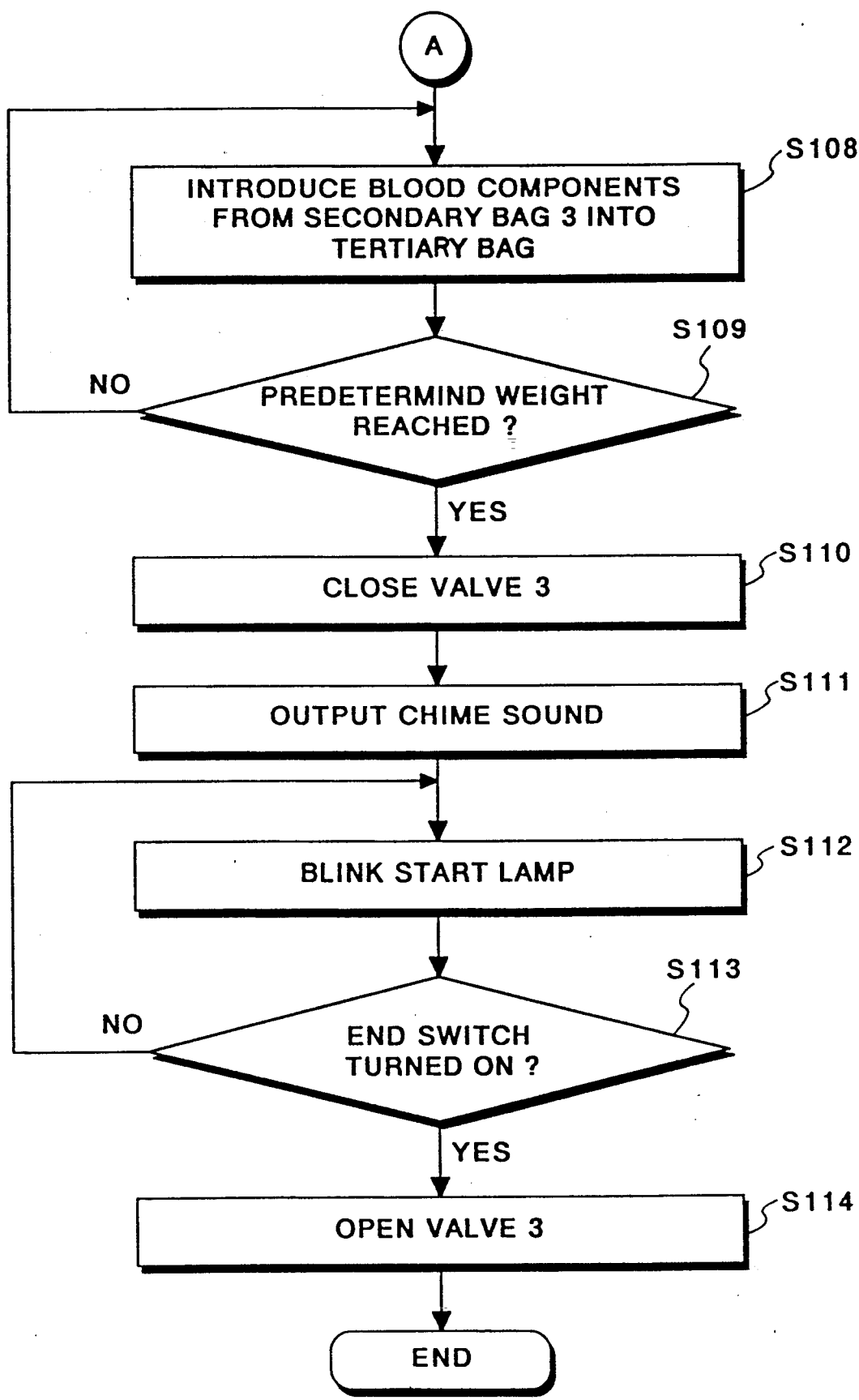
Figure 8:
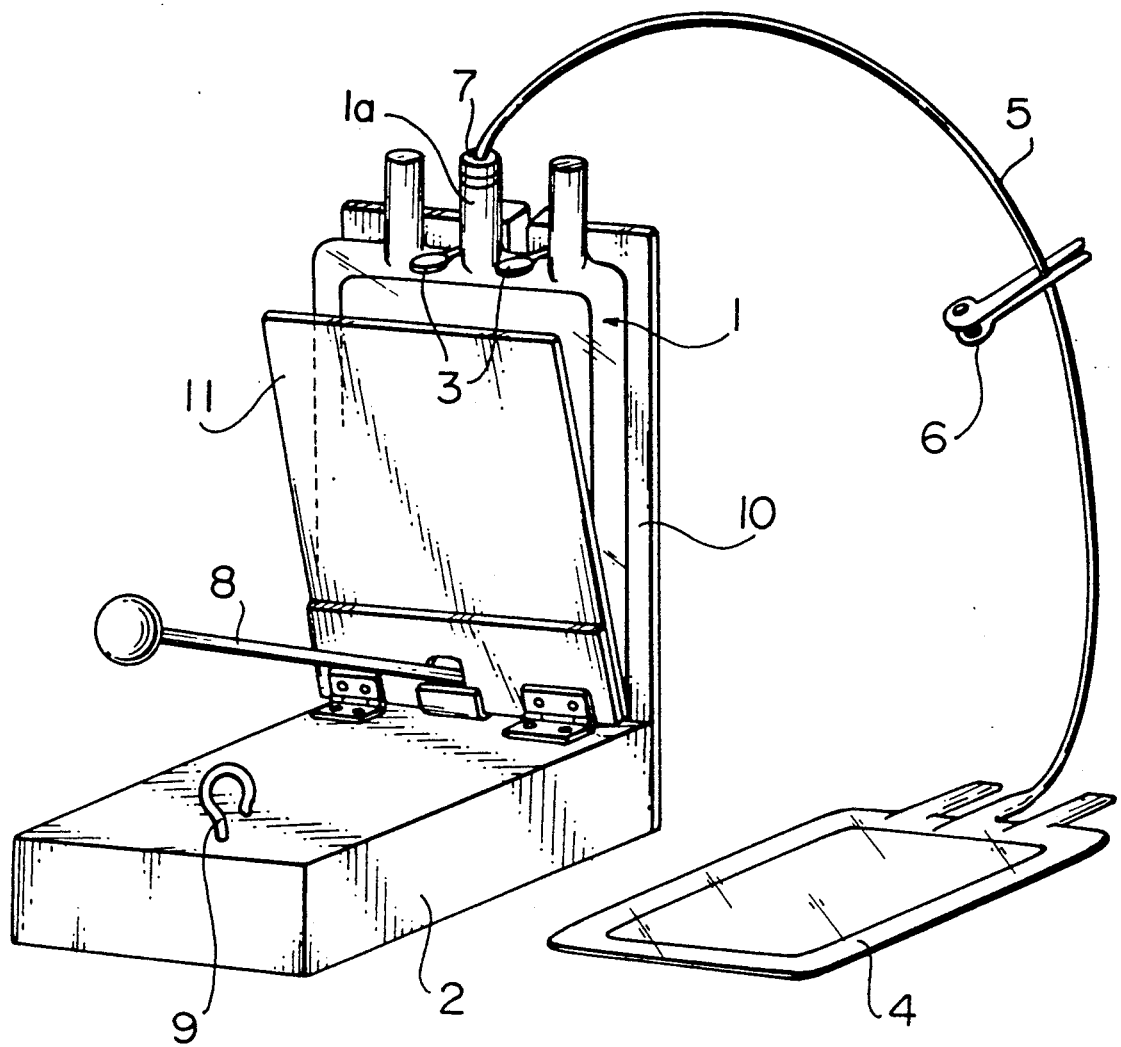
FIG. 8 is a diagram of the appearance of a conventional blood separator.

An example of such a separation process based on weight measurement will be described below with reference to the flow charts of FIGS. 7A and 7B.

In step S100, a key "3" of the select switch 36 is depressed to select a third sequence. In step 101, the secondary bag 3 (53) in the state shown in FIG. 5 is set at the pressurizing plate 21, and the tertiary bag (54) is placed on the measurement plate 23. In step S102, communication is provided between the secondary bag 3 (53) and the tertiary bag (54) by a tube which is clamped by the clamp valve 3 (35) at its intermediate portion. In step S103, the start switch 37 is depressed and turned on. The control section 100 detects this operation, the process immediately proceeds to step 104, and the valve control section 110 is controlled so as to close the clamp valve 3 (35). Then, in step S105, the weight of the tertiary bag (54) placed on the measurement plate 23 is measured and a measured value is stored in the RAM 113. In step S106, the pressurizing cylinder control section 101 is controlled so as to stop actuation of the pressurizing cylinder, so that the pressurizing plate 21 is pressed against the secondary bag 3 (53) by the force of the pressurizing plate spring. In step S107, the clamp valve 3 (35) is opened and, in step S108, the blood content of the secondary bag 3 (53) is transported to the tertiary bag (54) by the pressing with the pressurizing plate 21.

In step S109, the weight of the tertiary bag (54) is monitored by being read from the weight conversion section 106, and is checked to determine whether or not the weight of the tertiary bag has been increased to a predetermined value designated from the program cassette 200 by transportation of a predetermined quantity (e.g., 40 g). After transportation of the predetermined quantity has been completed, the process proceeds to step S110. In steps S110 to S114, the same processing as steps S59 to S63 of FIG. 6 is executed.

As described above, the blood separator in accordance with this embodiment operates on the basis of a multi-bag system for making blood component preparations by centrifugation (e.g., a double-bag system, triple-bag system, a quadruple-bag system or SAG bag system) and automatically separates the blood component parts (red and white corpuscles, platelets and plasma) as desired. The present invention thus eliminates the need for any manual separating operation such as that required in the conventional system, thereby reducing the burdens imposed on the operator.

Moreover, the present invention enables one unit to have various functions, i.e., functions as a separation stand, a function for detecting an interface between the blood components, a clamping function (tube sealing function) and a weight measuring function, thereby enabling construction of a blood separator having a reduced size.

The blood separator of the present invention can be operated by any person to separate the blood components uniformly, although conventionally the operator needs to be skilled in controlling the detection of an interface between the blood components and the quantity (weight) of each blood component part as well as have quick perceptions.

As described above, the blood separator of the present invention is, though reduced in size, capable of automatically separating desired quantities of blood components without requiring a high degree of skill and intuition.

Also, the blood separator of the present invention is, though reduced in size, capable of enabling the operator to select the height at which the interface is detected, as well as automatically separating desired quantities of blood components without requiring a high degree of skill and intuition.

What is claimed is:

1. A blood separator for separating blood components from a blood bag into separation bags, comprising:
   blood bag pressurizing means for retaining and controllably pressurizing the blood bag at a predetermined pressure after centrifugation;
   bag retaining means for retaining at least two of said separation bags;
   tube means for connecting the at least two of said separation bags with said blood bag to receive separated blood components;
   limiting means, provided at intermediate portions of said tube means between said blood bag and said separation bags retained by said retaining means, for limiting liquid flow in said tube means;
   detection means for detecting an interface level between the blood components in said blood bag retained by said blood bag pressurizing means;
   moving means for moving said detection means relative to said blood bag pressurizing means; and
   control means for controlling said limiting means while receiving detection information supplied as an item of control information from said detection means.

2. A blood separator according to claim 1, wherein said detection means includes
   light emitting means for emitting light,
   light receiving means for receiving as transmitted light, the light emitted from said light emitting means and transmitted through said blood bag, and
   means for detecting the interface level from a change in intensity of the transmitted light due to a difference between compositions of the blood components in said blood bag.

3. A blood separator according to claim 1, wherein said tube means includes an outlet tube extending from said blood bag and diverging at a divergence point into a tube connecting with a first one of said separation bags and another tube connecting with a second one of said separation bags, and wherein said limiting means limits the liquid flow between the divergence point and said separation bags.

4. A blood separator according to claim 1, wherein a position of at least one of said bag retaining means for retaining said separation bags is higher than said blood bag pressurizing means.

5. A blood separator according to claim 4, wherein a separated blood component received by one of said separation bags retained at the position higher than said blood bag pressurizing means can be returned to said blood bag.

6. A blood separator for separating blood components from a blood bag into separation bags, comprising:

blood bag pressurizing means for retaining and controllably pressurizing said blood bag at a predetermined pressure after centrifugation;

tube means for connecting said separation bags with said blood bag to receive separated blood components;

a plurality of retention/measurement means, each provided for one of said separation bags, for measuring the weight of and for holding said separation bags;

limiting means, provided at intermediate portions of said tube means between said blood bag and said separation bags, for limiting liquid flow in said tube means;

detection means for detecting an interface level between the blood components in said blood bag retained by said blood bag pressurizing means;

moving means for moving said detection means relative to said blood bag; and control means for controlling said limiting means while receiving, as control information, at least one of detection information from said detection means and measurement information from said retention/measurement means.

7. A blood separator according to claim 6, wherein said detection means includes light emitting means for emitting light, light receiving means for receiving as transmitted light, the light emitted from said light emitting means and transmitted through said blood bag, and means for detecting the interface level from a change in intensity of the transmitted light due to a difference between compositions of the blood components in said blood bag.

8. A blood separator according to claim 6, wherein said tube means includes an outlet tube extending from said blood bag and diverging at a divergence point into a tube connecting with a first one of said separation bags and another tube connecting with a second one of said separation bags, and wherein said limiting means limits the liquid flow between the divergence point and said separation bags.

9. A blood separator according to claim 6, wherein a position of at least one of said bag retaining means for retaining said separation bags is higher than said blood bag pressurizing means.

10. A blood separator according to claim 9, wherein a separated blood component received by one of said separation bags retained at the position higher than said blood bag pressurizing means can be returned to said blood bag.

11. A blood separator according to claim 10, wherein said control means includes means for controlling rate of flow of the liquid flow based upon said measurement information from one of said retention/measurement means when said separated blood component is returned.

12. A blood separator according to claim 6, further comprising a compact mounting structure for mounting said blood bag pressurizing means, said tube means, said retention/measurement means, said limiting means, said detection means, said moving means and said control means.

* * * * *

UNITED STATES PATENT AND TRADEMARK OFFICE
CERTIFICATE OF CORRECTION

PATENT NO. : 5,045,185

DATED : September 3, 1991

INVENTOR(S) : Ohnaka et al.

It is certified that error appears in the above-identified patent and that said Letters Patent is hereby corrected as shown below:

On title page, item
    [75], line 2, "Tatsumiko Kawaoka" should be --Tatsuhiko Kawaoka--.

Col. 1, line 48, "star" should be --start--.

Col. 3, line 16, "embodiment" should be --embodiment;--.

Signed and Sealed this

Thirtieth Day of March, 1993

*Attest:*

STEPHEN G. KUNIN

*Attesting Officer*     *Acting Commissioner of Patents and Trademarks*